(12) United States Patent
Huttunen et al.

(10) Patent No.: US 11,911,181 B1
(45) Date of Patent: Feb. 27, 2024

(54) FLEXIBLE WEARABLE RING DEVICE

(71) Applicant: Oura Health Oy, Oulu (FI)

(72) Inventors: Heikki Juhani Huttunen, Oulu (FI);
Teemu Juhani Haverinen, Oulu (FI);
Jouni Juhani Huopana, Oulu (FI);
Antti Kalevi Lämsä, Oulu (FI); Sami Sakari Ihme, Oulu (FI); Jukka Tapani Mäkinen, Oulu (FI)

(73) Assignee: Oura Health Oy, Oulu (FI)

( * ) Notice: Subject to any disclaimer, the term of this patent is extended or adjusted under 35 U.S.C. 154(b) by 0 days.

(21) Appl. No.: 18/177,608

(22) Filed: Mar. 2, 2023

(51) Int. Cl.
*A61B 5/00* (2006.01)
*A61B 5/0205* (2006.01)

(52) U.S. Cl.
CPC .......... *A61B 5/6826* (2013.01); *A61B 5/0002* (2013.01); *A61B 5/0205* (2013.01); *A61B 5/0059* (2013.01); *A61B 2560/0214* (2013.01); *A61B 2562/164* (2013.01)

(58) Field of Classification Search
CPC ... A61B 5/6826; A61B 5/0002; A61B 5/0205; A61B 5/0059; A61B 2560/0214; A61B 2562/164
See application file for complete search history.

(56) References Cited

U.S. PATENT DOCUMENTS

| | | |
|---|---|---|
| 9,711,060 B1 | 7/2017 | Lusted et al. |
| 2009/0088007 A1* | 4/2009 | Tsai ........................ H05K 3/365 439/67 |
| 2015/0220109 A1* | 8/2015 | von Badinski ......... H02S 99/00 368/10 |
| 2015/0342529 A1* | 12/2015 | Gassoway ............ A61B 5/6831 600/479 |
| 2018/0020977 A1* | 1/2018 | Li ........................ A61B 5/6802 600/384 |
| 2019/0183364 A1* | 6/2019 | Basu ..................... A61B 5/7203 |
| 2021/0177353 A1 | 6/2021 | Bhagat et al. |
| 2022/0394370 A1 | 12/2022 | Sarbou |

FOREIGN PATENT DOCUMENTS

CN 108143427 A 6/2018

OTHER PUBLICATIONS

International Search Report and Written Opinion—PCT/US2023/063737—ISA/EPO—dated Oct. 9, 2023.

* cited by examiner

*Primary Examiner* — Brian T Gedeon
*Assistant Examiner* — Joshua Andrew Schum-Houck
(74) *Attorney, Agent, or Firm* — Holland & Hart LLP

(57) ABSTRACT

A wearable device is described. The wearable device may be constructed of one or more flexible materials, and may be referred to as a flexible wearable device. The flexible wearable device may include a flexible housing that is made of a material that is elastically deformable, where the flexible housing at least partially surrounds components of the flexible wearable device. The flexible housing may include apertures disposed within the surface of the flexible housing to enable light to be transmitted and received through the flexible housing. The flexible wearable device may also include a printed circuit board (PCB) disposed within the flexible housing (e.g., within a cavity formed by the flexible housing). The PCB may include sensors configured to acquire physiological data from a user by transmitting light and receiving light through the apertures. The PCB may be constructed of flexible regions that are elastically deformable.

19 Claims, 5 Drawing Sheets

FLEXIBLE WEARABLE RING DEVICE

FIELD OF TECHNOLOGY

The following relates to wearable devices and data processing, including a flexible wearable device.

BACKGROUND

Some wearable devices may be configured to collect physiological data from users, including temperature data, heart rate data, and the like. However, poor contact between a user's skin and one or more sensors of a wearable device may result in inaccurate measurements. Further, the wearable device may be manufactured from a non-flexible material, such as metal or a rigid plastic material, which may increase manufacturing cost and may be unsafe for a user to wear when performing one or more activities where the wearable device may be caught or snagged on objects such as heavy machinery.

DETAILED DESCRIPTION

Figure 1:
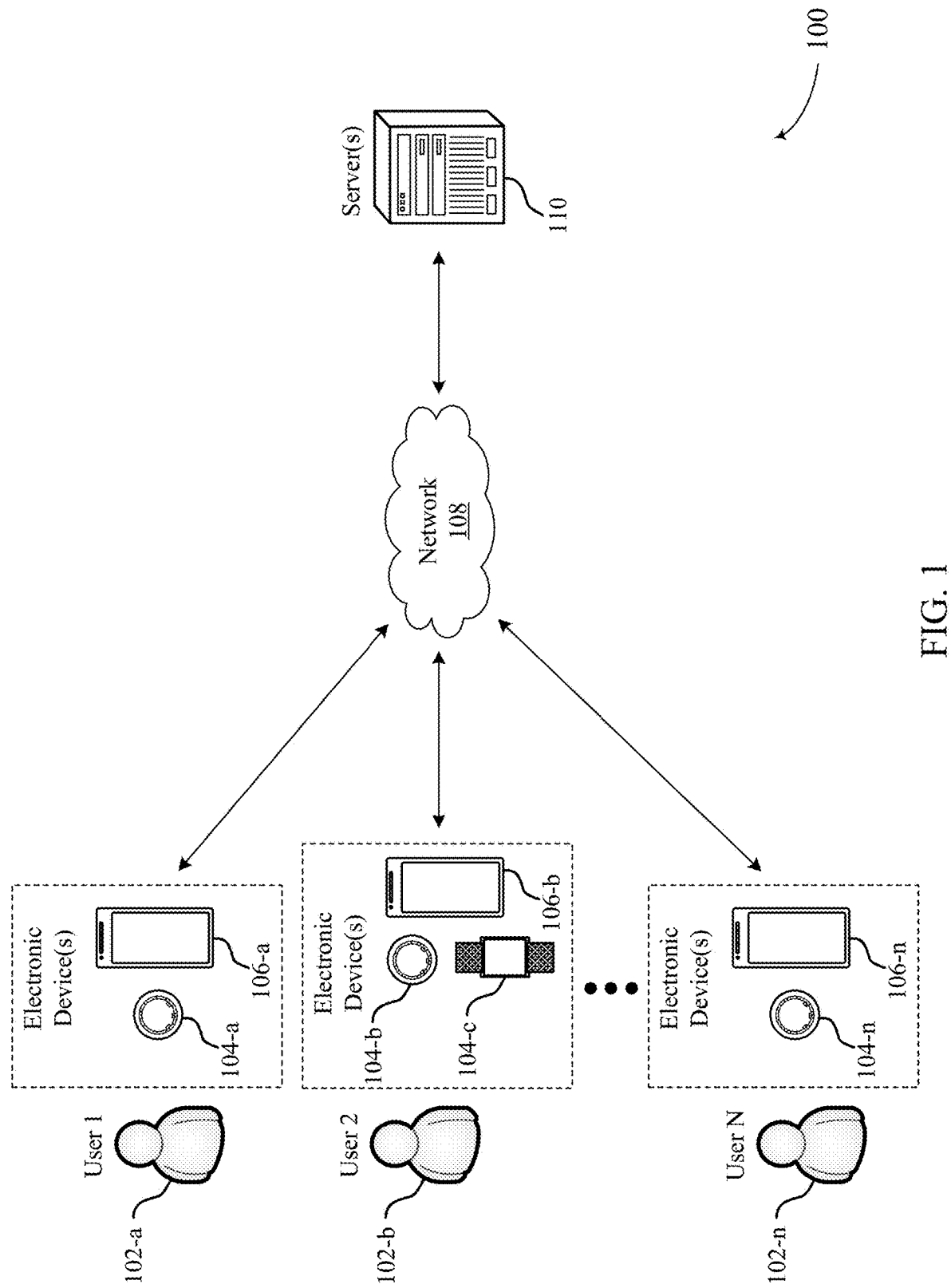
FIG. 1 illustrates an example of a system that supports flexible wearable devices in accordance with aspects of the present disclosure.

Some wearable devices may be configured to collect data from users associated with movement and other activities. For example, some wearable devices may be configured to continuously acquire physiological data associated with a user including temperature data, heart rate data, and the like. In order to track physiological data efficiently and accurately, a wearable device may be configured to collect data continuously while the user wears the device.

In some cases, there may be a gap between the skin of a user and a wearable device. For example, if the wearable device is a ring, pressure on the ring may create an air gap between the other side of the ring and the skin of the user due to a finger of the user being depressed against the ring. In some other examples, if the wearable device is worn on a wrist of a user, pressure on the device may create an air gap between the opposite side of the device and the skin of the user due to a wrist of the user being depressed against the wearable device. Additionally, or alternatively, the wearable device may be relatively large for a user, either due to the actual size of the wearable device or due to changing size of the user's tissue or fingers (e.g., fingers expanding/contracting based on hydration levels, weight gain/loss, pregnancy, etc.), which may create gaps between the wearable device and the skin of the user (e.g., ill-fitting ring). The gap may align with one or more sensors of the wearable device, such as one or more light emitting diodes (LEDs) and one or more respective photodetectors (PDs), which may create new optical interfaces between the skin of the user and the sensors (e.g., optical interfaces between the LEDs and photodetectors). The new optical interfaces may behave differently as compared to cases where there is good skin contact between the skin of the user and the sensors (e.g., may change a critical angle due to reflections, reduce perfusion index due to internal stray light, cause variations in distribution of light, and the like). The variation in optical interface may cause inaccurate readings from the sensors. In some cases, the wearable device may adjust a power of the sensors, such as increasing the brightness of an LED, to account for the variation in readings, which may increase power consumption at the wearable device. Taken together, these issues with wearable devices may result in inaccurate physiological data readings, which may lead to a distorted picture of the user's overall health, as well as increased power consumption and decreased battery life.

Additionally, some wearable devices may be manufactured from a non-flexible material, such as rigid metal and/or a plastic material that are designed to protect inner components of the wearable device. Such rigid materials may protect sensitive sensors and circuitry of the wearable device from damage that may be caused by water and other substances, dropping the wearable device, bumping into objects with the wearable device, and the like. However, such rigid materials may be susceptible to scratching and other minor damages that may detrimentally affect the aesthetic appearance of the wearable device. Further, such metal and plastic materials may be complex to manufacture, for example, due to manufacturing many different discrete sizes of the wearable device to improve user fit and thereby reduce any gaps that may occur between the wearable device and the skin of the user. However, manufacturing many different sizes of the wearable device, and manufacturing the wearable devices out of non-flexible materials, may be expensive and ill-suited for some users and use-cases.

In addition to increasing the complexity and cost of the manufacturing process, constructing wearable devices out of non-flexible materials may present comfort and/or safety concerns for the user (and damage to the wearable device) when the user performs one or more activities. For example, when working with machinery, a wearable device may become caught or snagged on the machinery, which may result in damage to the wearable device and serious injury to the user. In order to prevent such injuries, the user may remove the wearable device when performing some activities, such as working, lifting heavy weights, etc. However, removing the wearable device for one or more activities may result in a lack of physiological data readings for the time period when the user removes the wearable device, which may also lead to a distorted picture of the user's overall health.

Accordingly, aspects of the present disclosure are directed to flexible wearable devices. Flexible wearable devices may address many of the issues associated with conventional wearable devices. For example, a wearable device manufactured from a flexible material may improve an overall fit for the user by reducing a gap between the wearable device and skin of a user, reduce the cost and complexity of manufacturing the wearable device, and improve safety and comfort for one or more user activities while wearing the wearable device. In particular, flexible wearable devices may be able to deform to move with and conform to a user's tissue to improve the overall fit of the wearable device. Further, flexible wearable devices may be able to deform when they become caught or snagged on objects, thereby reducing safety risks to the user and potentially reducing damage to the wearable device. Moreover, flexible wearable devices may be able to expand and contract along with a user's tissue, thereby improving comfortability and enabling the devices to be used while weight lifting, climbing, and performing other hands-on activities.

For example, a wearable ring device of the present disclosure may include a flexible printed circuit board (PCB) disposed within a flexible housing that is manufactured of a material that is elastically deformable, such as an elastomer material. That is, the flexible housing may be able to deform (e.g., bend, flex, twist) in response to an exerted force, and may return to its original shape once the force is removed. Further, the flexible PCB may include one or more flexible regions that enable the PCB to bend and flex along with the flexible housing.

The ability of the wearable device to flex and bend may enable the wearable device to expand to fit a user (e.g., an appendage of the user that varies in size between users and/or over time), thereby improving contact between the sensors of the wearable device and the skin of the user and reducing the quantity of discrete sizes of the wearable device that are produced, which may in turn reduce manufacturing costs of the wearable device. Moreover, the material of the flexible housing may be more resistant to scratches as compared to rigid housings made of metal and plastic materials. Further, the ability of the flexible wearable device to elastically deform may improve a comfortability of the wearable devices, and reduce the likelihood of injury to the appendage of the user (e.g., in the event that the wearable device becomes caught on an object or pressed on by a relatively large force), thereby making the wearable device more suitable for a wide array of users and industries.

Aspects of the disclosure are initially described in the context of systems supporting physiological data collection from users via wearable devices. Additional aspects of the disclosure are described in the context of example wearable device diagrams. Aspects of the disclosure are further illustrated by and described with reference to apparatus diagrams, system diagrams, and flowcharts that relate to flexible wearable devices.

FIG. 1 illustrates an example of a system 100 that supports flexible wearable device in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some conventional wearable devices, there may be a gap between the skin of a user 102 and a wearable device 104. The gap may align with one or more sensors of the wearable device 104, which may cause variability and inaccuracy in the readings from the sensors. In some cases, the wearable device 104 may adjust a power of the sensors, to account for the variation in readings, which may increase power consumption at the wearable device 104. Taken together, these issues with wearable devices 104 may result in inaccurate physiological data readings, which may lead to a distorted picture of the user's overall health, as well as increased power consumption and decreased battery life.

Further, some conventional wearable devices 104 may be manufactured from a non-flexible material, such as rigid metal and/or a plastic material that are designed to protect inner components of the wearable device 104. However, such rigid materials may be susceptible to scratching and other minor damages that may detrimentally affect the aesthetic appearance of the wearable device 104. Further, such metal and plastic materials may be complex to manufacture, for example, due to manufacturing many different sizes of the wearable device 104 to reduce any gaps that may occur between the wearable device 104 and the skin of the user 102. However, manufacturing many different sizes of the wearable device 104 and manufacturing the wearable devices 104 out of the non-flexible material may be expensive.

In addition to increasing the complexity and cost of the manufacturing process, the user 102 may perform one or more activities in which having a wearable device 104 made of a non-flexible material may present a safety concern or may damage the wearable device 104 (operating machinery, performing a physical activity in which the wearable device may become trapped or in which a relatively large force is applied to the wearable device, may be at risk of electrical shock due to metal wearable device, etc.). However, removing the wearable device 104 for one or more activities may result in a lack of physiological data readings for the time period when the user 102 removes the wearable device 104, which may also lead to a distorted picture of the user's overall health.

Accordingly, a wearable device 104 of the present disclosure may be manufactured from a flexible material to reduce a gap between the wearable device 104 and skin of a user 102 of the wearable device 104, reduce the cost and complexity of manufacturing the wearable device 104, and improve safety for one or more user activities while wearing the wearable device 104.

For example, a wearable device 104 of the system 100 may include a flexible PCB disposed within a flexible housing that is manufactured of a material that is elastically deformable, such as an elastomer material. That is, the flexible housing may be able to deform (e.g., bend, flex, twist) in response to an exerted force, and may return to its original shape once the force is removed. Further, the flexible PCB may include one or more flexible regions that enable the PCB to bend and flex along with the flexible housing.

The ability of the wearable device 104 to flex and bend may enable the wearable device 104 to expand to fit a user 102 (e.g., an appendage of the user that varies in size between users and/or over time), thereby improving contact between the sensors of the wearable device 104 and the skin or of the user 102 and reducing the quantity of discrete sizes of the wearable device 104 that are produced, which may in turn reduce manufacturing costs of the wearable device 104. Moreover, the material of the flexible housing may be more resistant to scratches as compared to rigid housings made of metal and plastic materials. Further, the ability of the flexible material of the wearable device 104 to elastically deform may reduce the likelihood of injury to the appendage of the user 102 (e.g., in the event that the wearable device becomes caught on an object or pressed on by a relatively large force), thereby making the wearable device 104 more suitable for a wide array of users 102 and industries.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
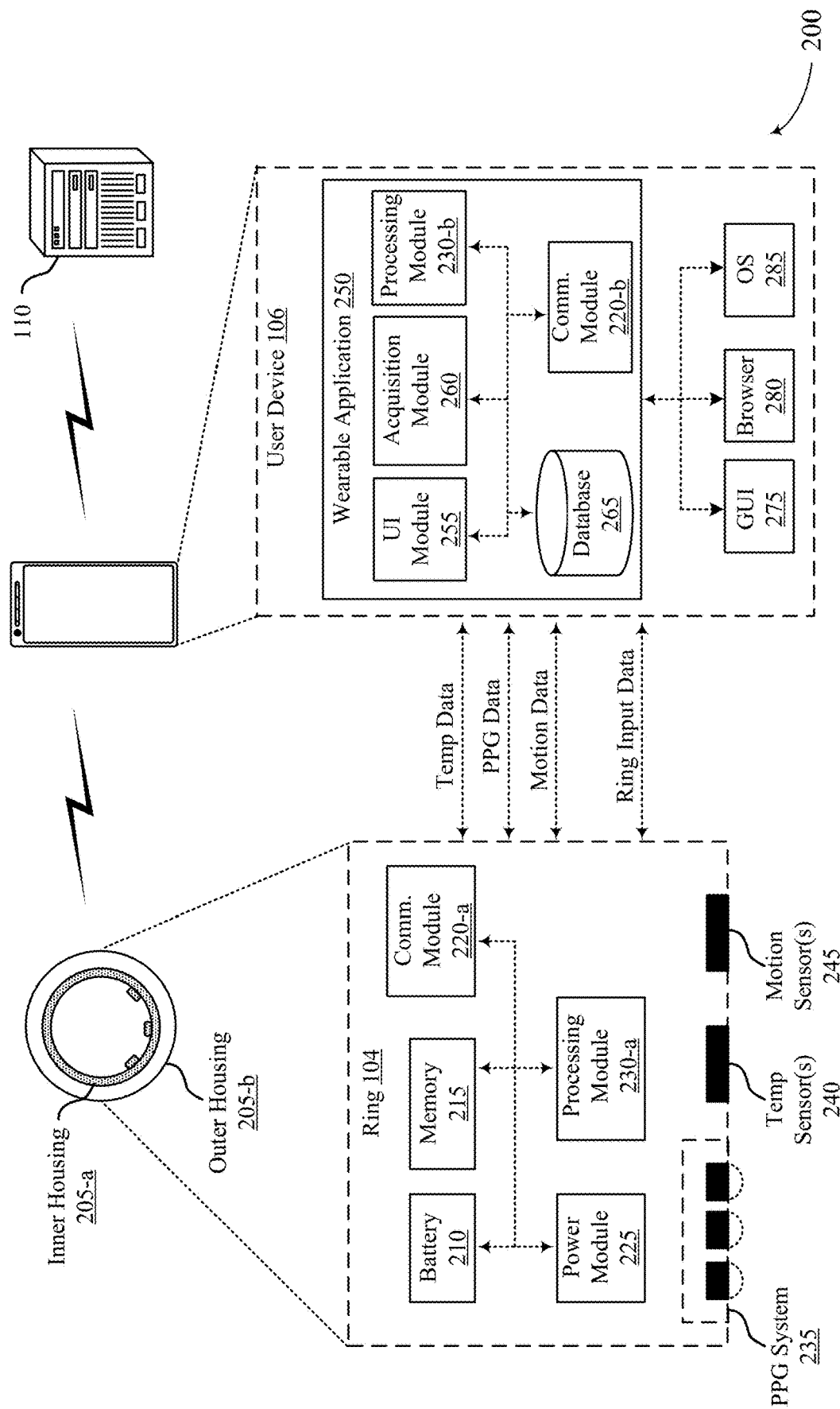
FIG. 2 illustrates an example of a system that supports flexible wearable devices in accordance with aspects of the present disclosure.

FIG. 2 illustrates an example of a system 200 that supports flexible wearable device in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, that may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-b. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more PCBs, such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support a wearable device 104 that is manufactured from a flexible material. A wearable device 104 may include a flexible PCB disposed within a flexible housing (e.g., a flexible inner housing 205-a and/or a flexible outer housing 205-b) that is manufactured of a material that is elastically deformable, such as an elastomer material. That is, the flexible housing may be able to deform (e.g., bend, flex, twist) in response to an exerted force, and may return to its original shape once the force is removed. Further, the flexible PCB may include one or more flexible regions that enable the PCB to bend and flex along with the flexible housing. For example, the PCB may flex or bend between one or more sensors (e.g., the PPG system 235, the temperature sensors 240, the motion sensors 245), may flex or bend between components of the battery 210 if the battery is segmented, or any other components.

The ability of the wearable device 104 to flex and bend may enable the wearable device 104 to expand to fit a user 102 (e.g., an appendage of the user that varies in size between users and/or over time), thereby improving contact between the sensors of the wearable device 104 and the skin or of the user 102 and reducing the quantity of discrete sizes of the wearable device 104 that are produced, which may in turn reduce manufacturing costs of the wearable device 104. Moreover, the material of the flexible housing may be more resistant to scratches as compared to rigid housings made of metal and plastic materials. Further, the ability of the flexible material of the wearable device 104 to elastically deform may reduce the likelihood of injury to the appendage of the user 102 (e.g., in the event that the wearable device becomes caught on an object or pressed on by a relatively large force), thereby making the wearable device 104 more suitable for a wide array of users 102 and industries.

Figure 3A:
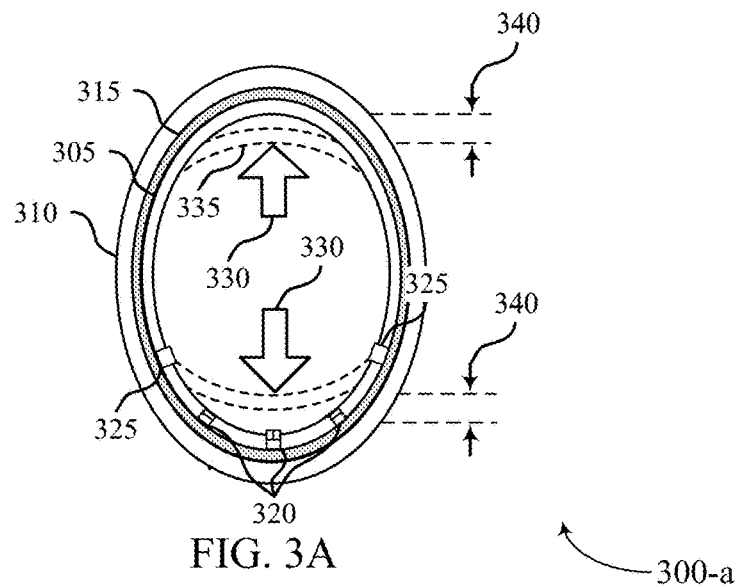
FIGS. 3A through 5B illustrates examples of wearable device diagrams that support flexible wearable devices in accordance with aspects of the present disclosure.
Figure 3B:
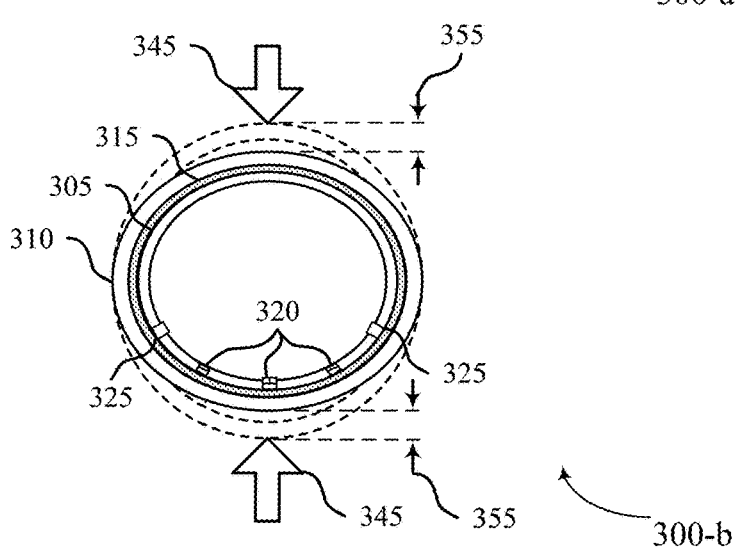
Figure 3C:
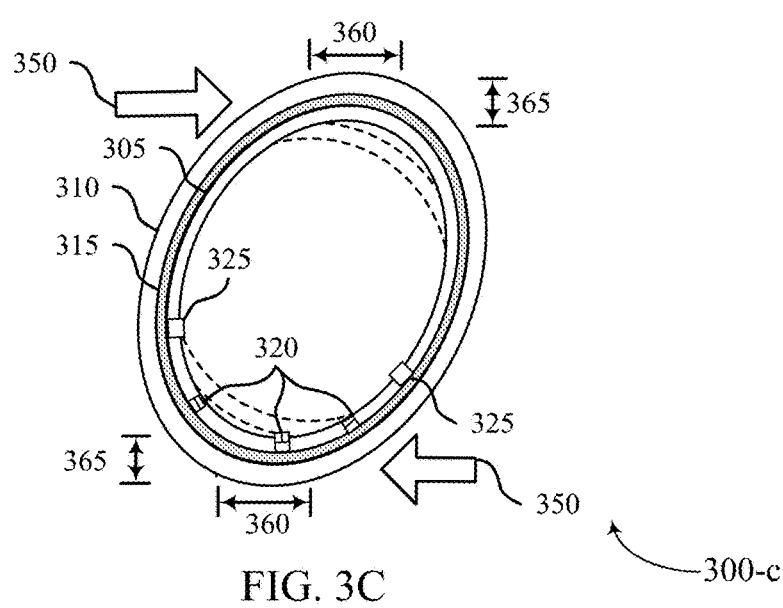

FIGS. 3A, 3B, and 3C illustrate an example of a wearable device diagram 300-a, a wearable device diagram 300-b, and a wearable device diagram 300-c that supports a flexible wearable device in accordance with aspects of the present disclosure. The wearable device diagram 300-a, the wearable device diagram 300-b, and the wearable device diagram 300-c may implement, or be implemented by, aspects of the system 100, system 200, or both. For example, the wearable device diagram 300-a, the wearable device diagram 300-b, and the wearable device diagram 300-c, may illustrate examples of wearable devices 104 as described with reference to FIG. 1.

Specifically, the wearable device diagram 300-a, the wearable device diagram 300-b, and the wearable device diagram 300-c may illustrate different elastic displacements/deformations of a flexible material of a wearable device 104 in response to forces applied in different directions. Although the wearable devices are illustrated as circular in FIGS. 3A through 3C, they may be any shape and any example of a wearable device (e.g., a ring, a watch or wristband, an armband, a necklace, and the like).

The wearable device 104 in wearable device diagram 300-a through wearable device diagram 300-c may include an inner housing 305 and an outer housing 310, which may be examples of an inner housing 205-a and an outer housing 205-b as described with reference to FIG. 2. In some cases, the inner housing 305 and the outer housing 310 may be a contiguous material formed from a single mold, as described in further detail with respect to FIGS. 4A through 5B. In some other cases, the inner housing 305 may be formed from a different mold/material than the outer housing 310, where the inner and outer housings may be joined together after they are formed, which is described in further detail with respect to FIGS. 4A through 5B.

Further, the wearable device in wearable device diagram 300-a through wearable device diagram 300-c may include an electronic substrate 315, such as a printed wiring board (PWB) or PCB. The PWB and/or the PCB may have both flexible and rigid sections. One or more sensors may be embedded in the electronic substrate 315. For the purposes of the present disclosure, the term "sensor" may be used to refer to a module including a pair of light-emitting and light-receiving components, such as a pair of LEDs and PDs. Additionally, in some cases, a "sensor" may include other components in addition to LEDs and PDs, such as lenses.

For example, the electronic substrate may include one or more light sources, such as LEDs 320, a laser diode (LD), or a VCSEL and one or more PDs 325. The LEDs 320 may emit light that is received by the PDs 325 to create optical channels for physiological data measurements. The wearable device 104 may include any number of LEDs, PDs, and respective optical channels for physiological data measurements. In some cases, LEDs 320 may include red LEDs, infrared LEDs, green LEDs, blue LEDs, or the like, which may emit light that is scattered and absorbed by the skin of a user of the wearable device. In general, the light sources may include any light-emitting components that are configured to emit light in any wavelength range (e.g., red light, yellow light, green light, infrared light, etc.). The PDs 325 may be configured to measure light from respective LEDs 320, which may be reflected by the skin and/or transmitted through the skin (e.g., reflective and/or transmissive measurements).

In some cases, the inner housing 305 may include a dome structure over the one or more LEDs 320, one or more PDs 325, or both. In some other cases, the inner housing 305 may include one or more windows (e.g., apertures) that enable the LEDs 320 to emit light through the inner housing 305, and that enable the PDs 325 to receive light through the inner housing 305. The wearable device 104 may use the light propagation from the LEDs 320 to the PDs 325 through tissue for physiological measurements, such as PPG and SpO2 measurements. That is, the wearable device may use light from an LED 320, which may include red and infrared wavelengths, to measure SpO2 and light from an LED 320, which may include green wavelengths, to measure PPG.

In some cases, the level of skin contact between the inner housing 305 of the wearable device 104 and the tissue of the user may impact the accuracy of the measurements. For example, with relatively good skin contact (e.g., when a gap between the inner housing 305 and the skin of a user is less than a threshold), a total internal reflection (TIR) critical angle may be relatively large over an optical interface between the wearable device 104 and skin of the user, and light out-coupling from the inner housing 305 may be relatively efficient. Thus, total light coupling losses from the LEDs 320 to the skin may be relatively low. Similarly, with relatively poor skin contact (e.g., when a gap between the inner housing 305 and the skin of a user is greater than a threshold), the TIR critical angle may be relatively small over the optical interface, and the light out-coupling from the inner housing 305 may be relatively inefficient. Thus, total light coupling loss from the LEDs 320 to the skin may be relatively high. The TIR is an optical phenomenon when light propagating inside optically clear material hits an interface between the material and another optical material with lower refractive index. The TIR critical angle may depend on the difference between refractive indices (n) of the LED 320 material and the material on the other side of the interface as well as other factors (e.g., polarization).

To reduce the likelihood of poor skin contact, the wearable device 104 may be manufactured with a flexible material, such that the wearable device 104 may stretch to accommodate a size of an appendage of the user. For example, if the wearable device 104 is a ring, the ring may stretch to fit multiple finger sizes, expand/contract to adjust to swelling/contracting finger sized (e.g., due to changes in hydration levels), and to enable the wearable device 104 to expand over a user's knuckle while maintaining a tight fit around the base of the user's finger. As illustrated in wearable device diagram 300-a, if a force 330 is applied to the inner housing 305 of the wearable device, such as if the appendage of the user is greater than the inner diameter of the wearable device 335, then the inner housing 305, the outer housing 310, the electronic substrate 315, or any combination thereof, may elastically deform (e.g., stretch) to accommodate the appendage of the user. In other words, the wearable device 104 may change from a first shape to a second shape in response to the applied force 330, which may be exerted, for example, by a user's swelling fingers. For example, the inner housing 305, the outer housing 310, the electronic substrate 315, or any combination thereof may deform by a displacement 340. The displacement 340 may be a function of the mechanical properties (e.g., stiffness) of the material of the inner housing 305, the outer housing 310, and the electronic substrate 315.

In some cases, such as if the wearable device 104 is made of a non-flexible material, the wearable device may fit a relatively small variation in size of an appendage of the user. However, the size of the appendage of each user may be different, such that many different sizes of wearable devices 104 are manufactured to accommodate each user. Comparatively, manufacturing the wearable device 104 of the flexible material may result in reduced manufacturing expense due to increasing the size tolerance of the wearable device 104. For example, a wearable device 104 made of a flexible material may fit a user with a diameter of the appendage anywhere from the inner diameter of the wearable device 335 to the diameter of the wearable device 104 after the displacement 340. Thus, fewer different sizes may be manufactured, which may result in fewer molds and may reduce manufacturing cost. Further, the ability of a wearable devices 104 to flex and bend may enable the wearable device 104 to expand to fit appendages of varying size (e.g., due to swelling and/or shrinking of an appendage), thereby improving contact between the LEDs 320, the PDs 325, and the skin of the user. Moreover, the ability of the wearable device 104 to flex, bend, expand, and contract may improve the overall fit and comfortability for the user.

In some examples, a user may perform an activity that puts force on the wearable device 104, such as a compression force 345 and/or a sheer force 350, as illustrated in the wearable device diagram 300-b and the wearable device diagram 300-c, respectively. For example, if the user lifts a heavy weight or operates machinery, the wearable device 104 may be a safety risk to the user in the case that the wearable device 104 damages tissue that is trapped between the wearable device 104 and the weight or the machinery. However, if the wearable device 104 is manufactured from a flexible material, the wearable device 104 may deform from the force to reduce, or avoid, injury to the user. The flexible material may be elastically deformable, such that the material may deform in response to an applied force, but will return to an original shape after the force is removed.

For example, if the wearable device 104 is a ring, and the user lifts a heavy weight, the wearable device 104 may deform by a displacement 355 from the compression force 345 to reduce a pressure applied by the wearable device 104 on the tissue of the user. Similarly, if the wearable device 104 becomes caught on an object (e.g., wedged between two objects, hooked on an object, or otherwise immobile relative to the object), and the user moves relative to the object, then the wearable device 104 may experience a sheer force 350 (e.g., stretching). If the wearable device 104 does not deform from the sheer force 350, then the wearable device 104 may damage the tissue of the user by applying pressure to the appendage of the user on the opposite side from the sheer force 350. However, if the wearable device 104 is manufactured from a flexible material, as described herein, then the wearable device 104 may deform by a horizontal displacement 360 and/or a vertical displacement 365, which may reduce the pressure applied to the appendage resulting from the sheer force 350. Further, the flexible material may be manufactured to fail at a lower force than a non-flexible material, such as metal or plastic, such that the wearable device 104 may break at a threshold force value (e.g., before damaging the tissue of the user).

In some examples, to prevent unexpected failure of the materials (e.g., breaking due to different forces applied to the material), the material properties of the inner housing 305, the outer housing 310, the electronic substrate 315, or any combination thereof may be configured for a value of force that causes material failure. For example, the inner housing 305 may have a different hardness and/or stiffness value than the outer housing 310. In some cases, the inner housing 305 may be less stiff than the outer housing 310, such as to prevent unexpected failure of the inner housing 305 (e.g., for a sheer force 350). Similarly, the material properties of the electronic substrate 315 may be selected to prevent damage to the electronic components, such as the LEDs 320, the PDs 325, and a battery. For example, the material of the electronic substrate 315 may have a localized increase in stiffness, such as around the battery.

In some examples, the outer housing 310, the inner housing 305, the electronic substrate 315, or any combination thereof may be partially rigid, such that the material may flex or bend to a defined value. In other words, the wearable device 104 may not be completely flexible, and may resist flexing after being deformed to the defined value (e.g., the force applied to elastically deform the wearable device increases as the displacement increases). In other words, wearable device 104 may exert a resistive force to the force 330, the compressive force 345, and/or the sheer force 350, where the resistive force exerted by the respective materials/components of the wearable device increases as the magnitude of the displacement (e.g., magnitude of the size/shape change) of the wearable device 104 increases.

In some implementations, the entire circumference of the wearable device 104 may be flexible. In additional or alternative implementations, only a portion of the circumference may be flexible. For example, in some cases, a top half of the wearable device 104 may be flexible (e.g., made out of a flexible material), where a bottom half may be rigid (or vice versa). Such implementations may enable the wearable device 104 to maintain the strength and aesthetics of a rigid device, while also exhibiting the flexibility and fit (e.g., comfort) of a flexible device.

Figure 4:
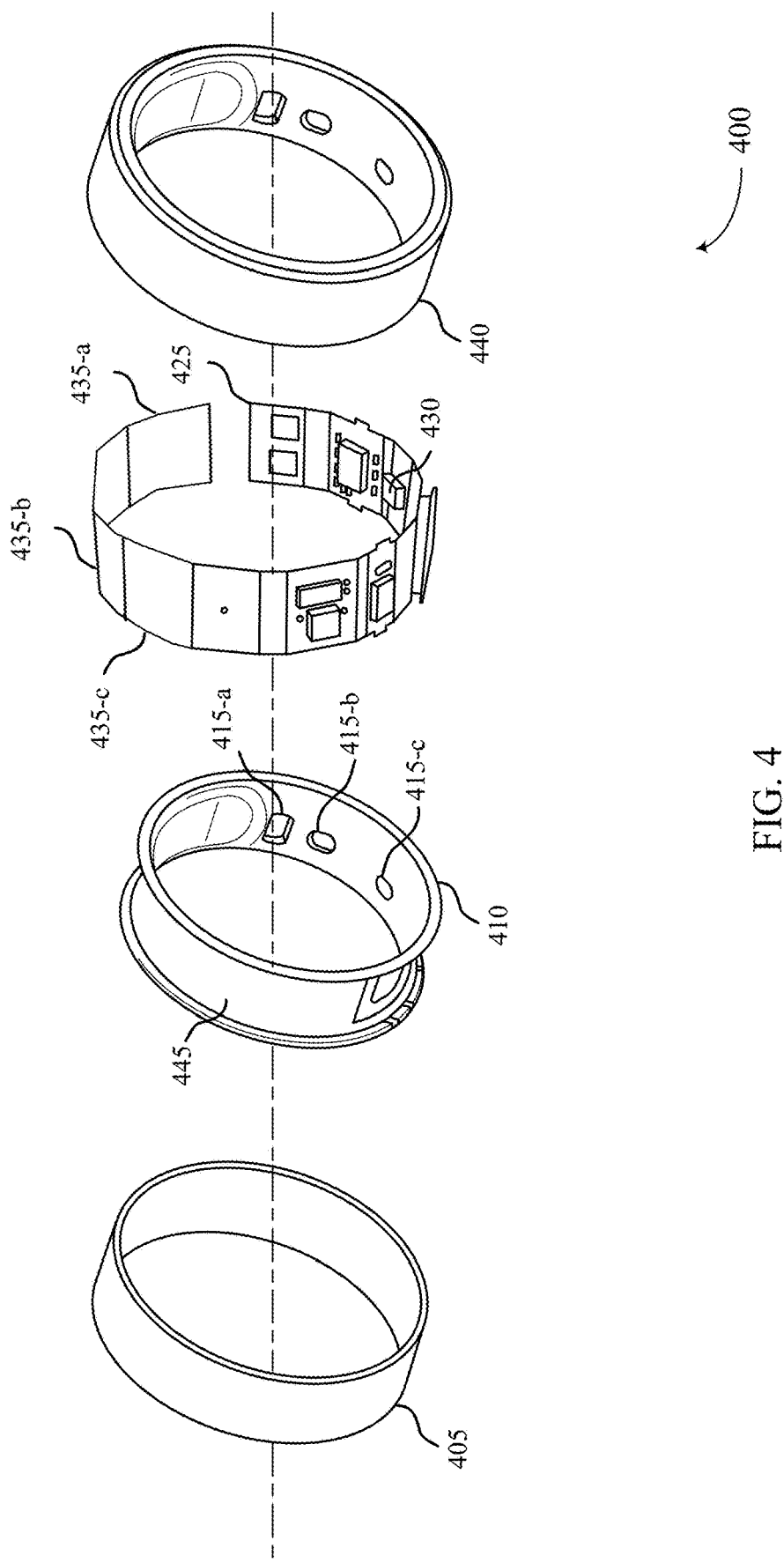

FIG. 4 illustrates an example of a wearable device diagram 400 that supports a flexible wearable device in accordance with aspects of the present disclosure. The wearable device diagram 400 may implement, or be implemented by, aspects of the system 100, system 200, the wearable device diagram 300-a through the wearable device diagram 300-c, or any combination thereof. For example, the wearable device diagram 400 may illustrate examples of wearable devices 104 as described with reference to FIG. 1. Specifically, the wearable device diagram 400 may illustrate a wearable device assembly that includes separate parts that are individually manufacturable. As such, each part of the wearable device diagram 400 may be customized or exchanged without compromising efficiency to manufacture the wearable ring device in its entirety. Although the wearable devices are illustrated as circular in FIG. 4, they may be any shape and any example of a wearable device (e.g., a ring, a watch or wristband, an armband, a necklace, and the like).

In some examples, the wearable device diagram 400 may include an outer housing 405, an inner housing 410, and a PCB 425. The inner housing 410 may be constructed from a first flexible material (e.g., an elastically deformable material), the outer housing 405 may be constructed from a second flexible material, and the PCB may be constructed from a third flexible material, where the flexible materials have the same material properties or different material properties. For example, the flexible materials may include an epoxy material, a polymer material, a polyurethane material, a silicon material, a rubber material, an elastomer material, or the like. The respective components of the wearable device diagram 400 may be examples of the corresponding components shown and described in FIGS. 3A through 3C.

In some examples, the outer housing 405, the inner housing 410, the PCB 425, or any combination thereof, may be manufactured separately. For example, the outer housing 405 and the inner housing 410 may be manufactured from different molds, and then may be joined together (e.g., with the PCB 425) through a fusion process. In some other examples, the outer housing 405 and the inner housing 410 may be manufactured from a same mold, which may encompass the PCB 425 or may later be joined to the PCB 425. The color or material of the outer housing 405 and the inner housing 410 may be selected from a wide array of colors or materials.

The inner housing 410 and the outer housing 405 may be referred to as a flexible housing, where the flexible housing includes a cavity 445 that at least partially surrounds the components of the flexible wearable device (e.g., the components of the PCB 425). In some cases, the inner housing 410 may include a one or more apertures (e.g., an aperture 415-a, an aperture 415-b, an aperture 415-c, or any combination thereof) for one or more sensors 430 to perform physiological measurements of a user. The sensors 430 may include LEDs, PDs, or any other type of components. The apertures (e.g., the aperture 415-a, the aperture 415-b, the aperture 415-c, or any combination thereof) may be filled with a transparent material configured to enable transmission and reception of light through the apertures to and from the sensors 430. For example, the apertures may be covered, or filled, with a transparent epoxy material to enable transmission and/or reception of light. In some cases, the relative size of the apertures may be relatively small when compared to the flexible housing, such that the transparent material does not break or become separated from the apertures when the wearable device elastically deforms.

In some implementations, the inner housing 410, the outer housing 405, or both, may include components or features that couple to the PCB 425 in the correct radial orientation within the inner housing 410 (e.g., detents, grooves, protrusions, or the like along the inner edges of the inner housing 410). In other words, the PCB 425 may include a first set of locking components that engage with a second set of locking components of the flexible housing (e.g., inner housing 410 and/or outer housing 405) in a defined radial orientation that aligns the sensors 430 of the PCB 425 with the respective apertures 415 of the flexible housing.

Additionally, or alternatively, the inner housing 410, the outer housing 405, or both may be fused (e.g., using heat), or otherwise bonded, to the PCB 425, such as by fusing the elastically deformable material in the PCB 425 with the elastically deformable material of the inner housing 410. Thus, the PCB 425 may be disposed within the cavity 445 of the flexible housing, such that when the wearable device is elastically deformed, a surface of the PCB 425 and a surface of the flexible housing remain stationary with respect to one another. Coupling the surface of the PCB 425 to the surface of the flexible housing may prevent the PCB 425 from sliding around within the flexible housing when the wearable device is elastically deformed, thereby maintaining alignment between the sensors 430 of the PCB 425 and the apertures 415 of the flexible housing.

The PCB 425 may be a flexible PCB that includes one or more sensors 430 or electrical components and is coupled to one or more battery components, such as a battery component 435-a, a battery component 435-b, and a battery component 435-c. In some examples, the sensors 430 may be positioned asymmetrically within the PCB 425. For example, the sensors on the PCB 425 may include a first light-emitting component (e.g., a first LED) positioned relative to the inner housing 410 at a first radial position, a second light-emitting component (e.g., a second LED) positioned relative to the inner housing 410 at a second radial position, and a third light-emitting component (e.g., a third LED) positioned relative to the inner housing 410 at a third radial position. If the sensors are positioned asymmetrically, the first radial position and the third radial position may define a segment of the inner housing 410 between the first radial position and the second radial position, where the third radial position is different from a radial midpoint of the segment.

In some examples, the battery of the wearable device may be segmented into any quantity of segments or components (e.g., the battery component 435-a, the battery component 435-b, and the battery component 435-c). The battery components may be separated by a flexible material (e.g., flexible portions coupling the respective battery segments/components) to provide for the battery to elastically deform with the flexible housing of the wearable device. The material between the battery components may be configured to couple the battery segments electrically and structurally to one another. Each battery component may be constructed of a flexible battery or a non-flexible battery (e.g., a coin battery). In some other examples, the battery of the wearable device may be a single unit, in which case the battery may be constructed of a flexible material.

In some cases, the PCB 425 may include one or more radio frequency components for wireless communications. The radio frequency components may be electrically coupled with the sensors 430. In some examples, the flexible material may enable wireless signals (e.g., near field communication (NFC) signals, Bluetooth signals, or both) to be communicated through the flexible housing to and from the one or more radio frequency components. In some cases, the flexible material of the wearable device may enable wireless signals to be communicated through the flexible housing to and from the radio frequency components with improved efficiency and reliability as compared to non-flexible materials (e.g., metals, plastics) associated with some conventional wearable devices. The wearable device 440 shown in FIG. 4 may illustrate the final form of the ring wearable assembly, including the outer housing 405, the inner housing 410, and the PCB 425.

Figure 5A:
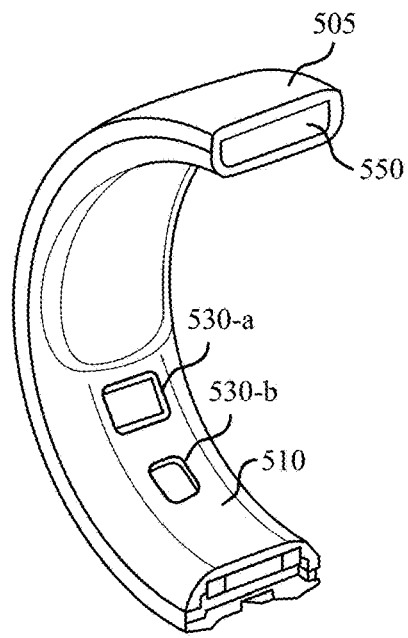
Figure 5B:
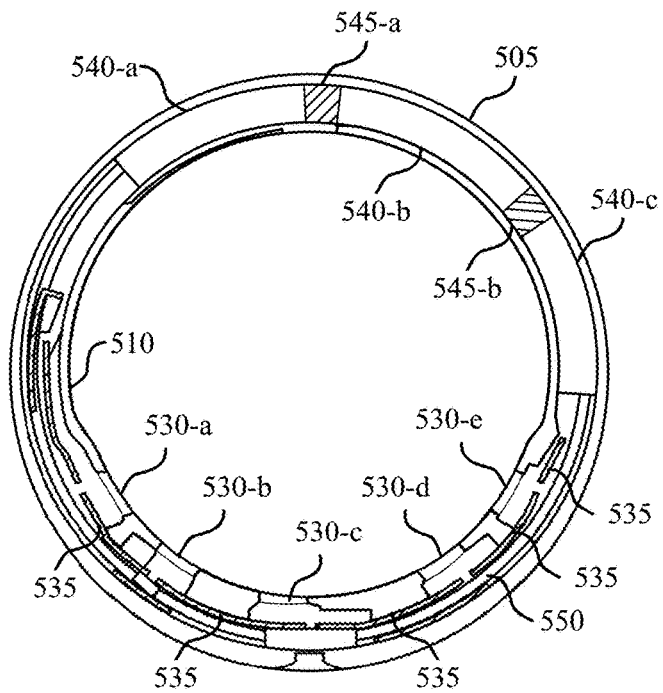

FIGS. 5A and 5B illustrate examples of a wearable device diagram 500-a and a wearable device diagram 500-b that supports a flexible wearable device in accordance with aspects of the present disclosure. The wearable device diagram 500-a and the wearable device diagram 500-b may implement, or be implemented by, aspects of the system 100, system 200, the wearable device diagram 300-a through the wearable device diagram 400, or any combination thereof. For example, the wearable device diagram 500-a and the wearable device diagram 500-b may illustrate examples of wearable devices 104 as described with reference to FIGS. 1-4. Specifically, the wearable device diagram 500-a and the wearable device diagram 500-b may illustrate a cross section of a flexible wearable device as described with reference to FIGS. 3A, 3B, 3C, and 4. Although the wearable devices are illustrated as circular in FIGS. 5A and 5B, they may be any shape and any example of a wearable device (e.g., a ring, a watch or wristband, an armband, a necklace, and the like).

In some examples, the wearable device may include the inner housing 510 and an outer housing 505, which may be made of a flexible material. For example, the flexible material may include an epoxy material, a polymer material, a polyurethane material, a silicon material, a rubber material, an elastomer material, or the like. The inner housing 510 may have the same or different material properties as the outer housing 505. In some cases, the inner housing 510 and the outer housing 505 may be made from a single mold, such that they are one contiguous material. In some other cases, the inner housing 510 and the outer housing 505 may be made from separate molds/materials, and may be bonded or fused together. For example, the inner housing 510 and the outer housing 505 may be fused together with heat. In some other examples, a sealing material may lock the outer housing 505 to the inner housing 510. The sealing material may include an epoxy, a pressure-fit component, and the like. Additionally, or alternatively, the sealing material may include the flexible material of the inner housing 510, the outer housing 505, or both.

The inner housing 510 may include a plurality of apertures (e.g., aperture 530-a, aperture 530-b, aperture 530-c, aperture 530-d, and aperture 530-e). The apertures may act as pathways from the sensors of the PCB 535 of the wearable device to finger tissue when worn by the user. The apertures (e.g., aperture 530-a, aperture 530-b, aperture 530-c, aperture 530-d, and aperture 530-e, and other apertures) may be included within the inner circumferential surface of the inner housing 510.

The wearable device diagram 500-b depicts a PCB 535 positioned within an internal cavity 550 of the wearable device and system described with reference to FIGS. 3A, 3B, and 4, illustrating the PCB 535 coupled to the inner housing 510. By positioning the PCB 535 in the cavity 550 defined by the inner housing 510 and the outer housing 505 as illustrated in the wearable device diagram 500-b, sensors of the PCB 535 may be contained within the confines of the inner circumference of the inner housing 510. In some cases, the PCB 535 may be coupled to the inner housing 510 by a bonding agent or fusion to the material of the inner housing 510. In some other cases, the inner housing 510 and the outer housing 505 may be molded over the PCB.

In some examples, sensors of the PCB 535 may align with the apertures 530 of the inner housing 510 such that the sensors may transmit and receive signals (e.g., light) to or from the finger tissue through the apertures 530. In some examples, the location of the apertures 530 may be based on the location of the sensors on the PCB 535. For instance, if the location of the sensors is predefined and fixed on the PCB 535, the apertures may be cut or molded into the inner housing 510 such that the apertures 530 align with the sensors on the inner housing 510. Additionally, or alternatively, the location of the sensors on the PCB 535 may be based on the location of the apertures 530. For instance, if the location of the apertures 530 is predefined and fixed on the PCB 535, the PCB 535 may position the sensors on the inner housing 510 such that the sensors align with the apertures 530.

The wearable device may include any quantity of sensors that may be distributed along the PCB 535 at any assortment of locations. That is, the sensors on the PCB 535 may vary in quantity and be spread through the wearable device on the PCB 535. As such, the quantity and positioning of the apertures 530 may not be limited to that of aperture 530-a, aperture 530-b, aperture 530-c, aperture 530-d, and aperture 530-e. Additionally, or alternatively, the quantity and positioning of the sensors on the PCB 535 may be variable.

In some examples, the battery of the wearable device may be split into multiple battery components or segments, such as a battery component 540-a, a battery component 540-b, and a battery component 540-c. The battery and/or battery components may be flexible or solid batteries. For example, if the battery is a single battery, the battery may be flexible to accommodate the elastic deformation of the wearable device. In some other examples, if the battery is segmented into battery components, the wearable device may include flexible material between each battery component, where the battery components 540 themselves may be solid batteries (e.g., coin batteries). For example, there may be a flexible material 545-a between the battery component 540-a and the battery component 540-b and a flexible material 545-b between the battery component 540-b and the battery component 540-c. The flexible material 545-a and the flexible material 545-b may have a relatively high stiffness value compared to the material of the inner housing 510 and the outer housing 505 (e.g., to prevent a battery component from flexing or bending to a point of failure). In such cases, the flexible material 545 may be configured to mechanically (e.g., structurally) and electrically couple the battery components 540 (e.g., battery segments) to one another.

The wearable device made from the flexible material may have a tighter, improved fit on the user's finger, with a decreased risk of loss of skin contact when impacted by external forces. Further, the molds for a flexible material may be less expensive, and the wearable device may fit an increased size range (e.g., the flexible wearable device may expand and contract to fit a wide array of discrete finger sizes), thereby simplifying and reducing cost of the manufacturing process for the wearable device.

It should be noted that the features described above describe possible implementations, and that other implementations are possible. Furthermore, aspects from two or more of the features may be combined.

A flexible wearable device is described. The flexible wearable device may include a flexible housing comprising a flexible material that is elastically deformable, wherein the flexible housing comprises, a cavity configured to at least partially surround one or more components of the flexible wearable device, a plurality of apertures disposed within a surface of the flexible housing, wherein the plurality of apertures are coupled with the cavity, a PCB disposed within the cavity, wherein the PCB comprises, a plurality of sensors configured to acquire physiological data from a user based at least in part on light transmitted and received through the plurality of apertures, and one or more flexible regions that are elastically deformable.

In some examples, the flexible wearable device includes a molded inner housing component including the flexible material, wherein the plurality of apertures may be disposed within the surface of the molded inner housing component and a molded outer housing component coupled with the molded inner housing component to form the cavity, wherein the molded outer housing component includes the flexible material, an additional flexible material, or both.

In some examples, the flexible wearable device includes a battery apparatus that may be electrically coupled with the plurality of sensors, wherein the battery apparatus comprises, a plurality of battery segments, and one or more connection segments that may be configured to electrically and structurally couple the plurality of battery segments to one another, wherein the one or more connection segments may be elastically deformable.

In some examples, the battery apparatus may be disposed on the PCB such that the one or more connection segments of the battery apparatus may be aligned with the one or more flexible regions of the PCB.

In some examples, the flexible wearable device may be configured to elastically deform from a first shape to at least a second shape in response to a force applied to the flexible wearable device, the flexible material, the one or more flexible regions, or both, may be configured to exert a resistive force against the force applied to the flexible wearable device, and a magnitude of the resistive force increases as the flexible wearable device may be elastically deformed from the first shape to the second shape.

In some examples, the flexible housing may be molded over the PCB such that at least one surface of the PCB may be bonded to at least one surface of the flexible housing that defines at least a portion of the cavity.

In some examples, the PCB may be embedded within the cavity and bonded to the flexible housing such that, when the flexible wearable device may be elastically deformed from a first shape to a second shape, the at least one surface of the PCB and the at least one surface of the flexible housing remain stationary with respect to one another.

In some examples, the flexible wearable device includes a transparent material disposed within the plurality of apertures, wherein the transparent material may be configured to enable transmission and reception of light through the plurality of apertures to and from the plurality of sensors.

In some examples, the flexible material comprises an epoxy material, a polymer material, a polyurethane material, a silicon material, a rubber material, an elastomer material, or any combination thereof.

In some examples, the flexible housing and the one or more flexible regions of the PCB may be elastically deformable in response to both a compressive force and a stretching force.

In some examples, the flexible wearable device includes one or more radio frequency components configured to perform wireless communications, the one or more radio frequency components electrically coupled with the plurality of sensors, wherein the flexible material may be configured to enable wireless signals to be communicated through the flexible housing to and from the one or more radio frequency components.

In some examples, the wireless signals comprise NFC signals, Bluetooth signals, or both.

In some examples, the flexible wearable device comprises a flexible wearable ring device, the flexible housing comprises a flexible ring-shaped housing, and the cavity comprises a ring-shaped cavity that extends at least partially around the flexible ring-shaped housing.

In some examples, the flexible wearable device comprises a flexible wearable ring device, the plurality of apertures may be disposed within an inner circumferential surface of the flexible ring-shaped housing.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:
1. A flexible wearable device, comprising:
a flexible housing comprising a flexible material that is elastically deformable and that at least partially surrounds one or more components of the flexible wearable device, wherein the flexible housing comprises:
an inner housing component associated with a first stiffness;
an outer housing component associated with a second stiffness that is different from the first stiffness;

a plurality of apertures disposed within a surface of the flexible housing; and a printed circuit board disposed within the flexible housing, wherein the printed circuit board comprises:

a plurality of sensors configured to acquire physiological data from a user based at least in part on light transmitted and received through the plurality of apertures; and one or more flexible regions that are elastically deformable.

2. The flexible wearable device of claim 1, wherein the flexible housing comprises:

a molded inner housing component including the flexible material, wherein the plurality of apertures are disposed within the surface of the molded inner housing component; and a molded outer housing component coupled with the molded inner housing component to form the flexible housing, wherein the molded outer housing component includes the flexible material, an additional flexible material, or both.

3. The flexible wearable device of claim 1, wherein the printed circuit board further comprises:

a battery apparatus that is electrically coupled with the plurality of sensors, wherein the battery apparatus comprises:

a plurality of battery segments; and one or more connection segments that are configured to electrically and structurally couple the plurality of battery segments to one another, wherein the one or more connection segments are elastically deformable.

4. The flexible wearable device of claim 3, wherein the battery apparatus is disposed on the printed circuit board such that the one or more connection segments of the battery apparatus are aligned with the one or more flexible regions of the printed circuit board.

5. The flexible wearable device of claim 1, wherein the flexible wearable device is configured to elastically deform from a first shape to at least a second shape in response to a force applied to the flexible wearable device, and wherein the flexible material, the one or more flexible regions, or both, are configured to exert a resistive force against the force applied to the flexible wearable device, wherein a magnitude of the resistive force increases as the flexible wearable device is elastically deformed from the first shape to the second shape.

6. The flexible wearable device of claim 1, wherein the flexible housing is molded over the printed circuit board such that at least one surface of the printed circuit board is bonded to at least one surface of the flexible housing.

7. The flexible wearable device of claim 6, wherein the printed circuit board is embedded within the flexible housing and bonded to the flexible housing such that, when the flexible wearable device is elastically deformed from a first shape to a second shape, the at least one surface of the printed circuit board and the at least one surface of the flexible housing remain stationary with respect to one another.

8. The flexible wearable device of claim 1, wherein the flexible housing further comprises:

a transparent material disposed within the plurality of apertures, wherein the transparent material is configured to enable transmission and reception of light through the plurality of apertures to and from the plurality of sensors.

9. The flexible wearable device of claim 1, wherein the flexible material comprises an epoxy material, a polymer material, a polyurethane material, a silicon material, a rubber material, an elastomer material, or any combination thereof.

10. The flexible wearable device of claim 1, wherein the flexible housing and the one or more flexible regions of the printed circuit board are elastically deformable in response to both a compressive force and a stretching force.

11. The flexible wearable device of claim 1, wherein the printed circuit board further comprises:

one or more radio frequency components configured to perform wireless communications, the one or more radio frequency components electrically coupled with the plurality of sensors, wherein the flexible material is configured to enable wireless signals to be communicated through the flexible housing to and from the one or more radio frequency components.

12. The flexible wearable device of claim 11, wherein the wireless signals comprise near field communication signals, Bluetooth signals, or both.

13. The flexible wearable device of claim 1, wherein the flexible wearable device comprises a flexible wearable ring device, the flexible housing comprises a flexible ring-shaped housing.

14. The flexible wearable device of claim 13, wherein the plurality of apertures are disposed within an inner circumferential surface of the flexible ring-shaped housing.

15. The flexible wearable device of claim 1, wherein the inner housing component is associated with the first stiffness to prevent damage to one or more electrical components of the flexible wearable device.

16. The flexible wearable device of claim 1, wherein the inner housing component, the outer housing component, or both, are configured to exert a resistive force based at least in part on a deforming force exerted on the flexible wearable device, wherein a magnitude of the resistive force increases as a magnitude of displacement of the inner housing component, the outer housing component, or both, increases.

17. The flexible wearable device of claim 16, wherein the magnitude of the resistive force exerted by the inner housing component and the outer housing component is based at least in part on the first stiffness of the inner housing component and the second stiffness of the outer housing component.

18. The flexible wearable device of claim 1, wherein the printed circuit board further comprises:

a battery apparatus that is electrically coupled with the plurality of sensors, wherein the battery apparatus comprises:

a plurality of battery segments; and one or more connection segments that are configured to electrically and structurally couple the plurality of battery segments to one another, wherein the one or more connection segments are elastically deformable, and wherein the one or more connection segments exhibit a third stiffness that is greater than the first stiffness and the second stiffness.

19. A flexible wearable ring device, comprising:

a flexible housing comprising a flexible material that is elastically deformable and that at least partially surrounds one or more components of the flexible wearable ring device, wherein the flexible housing comprises:

a first portion associated with a first stiffness, wherein the first portion of the flexible housing spans a first radial portion around a circumference of the flexible wearable ring device, and wherein the first stiffness is selected based at least in part on one or more components positioned within the first radial portion of the flexible housing;

a second portion associated with a second stiffness that is different from the first stiffness, wherein the second portion of the flexible housing spans a second radial portion around the circumference of the flexible wearable ring device, and wherein the second stiffness is selected based at least in part on one or more additional components positioned within the second radial portion of the flexible housing;

a plurality of apertures disposed within a surface of the flexible housing; and a printed circuit board disposed within the flexible housing, wherein the printed circuit board comprises:

a plurality of sensors configured to acquire physiological data from a user based at least in part on light transmitted and received through the plurality of apertures; and one or more flexible regions that are elastically deformable.

\* \* \* \* \*